United States Patent

Yajima et al.

[11] Patent Number: 5,858,423
[45] Date of Patent: Jan. 12, 1999

[54] CHEWING GUM COMPOSITION CONTAINING GLIADIN AND TRANSGLUTAMINASE

[75] Inventors: Mizuo Yajima; Ryouta Katahira, both of Tokyo, Japan

[73] Assignee: Asama Chemical Co., Ltd., Tokyo, Japan

[21] Appl. No.: 627,544

[22] Filed: Apr. 4, 1996

Related U.S. Application Data

[63] Continuation of Ser. No. 342,617, Nov. 21, 1994, abandoned.

[30]    Foreign Application Priority Data

| Jun. 3, 1994 | [JP] | Japan | 6-144047 |
| Jun. 13, 1994 | [JP] | Japan | 6-153095 |
| Jul. 13, 1994 | [JP] | Japan | 6-183018 |
| Jul. 14, 1994 | [JP] | Japan | 6-184141 |
| Aug. 11, 1994 | [JP] | Japan | 6-209312 |
| Aug. 30, 1994 | [JP] | Japan | 6-227432 |

[51] Int. Cl.$^6$ .................................................. A23G 3/30
[52] U.S. Cl. .............................................. 426/3; 426/656
[58] Field of Search ...................... 426/3, 656, 425, 426/429, 436, 481, 655

[56]    References Cited

U.S. PATENT DOCUMENTS

| 1,700,387 | 1/1929 | Stetson | 426/3 |
|---|---|---|---|
| 2,469,861 | 5/1949 | Cohoe . | |
| 2,586,675 | 2/1952 | Lutz | 426/3 |
| 3,770,452 | 11/1973 | Finley | 426/190 |
| 3,832,472 | 8/1974 | Rodgers et al. | 426/148 |
| 3,956,515 | 5/1976 | Moore et al. | 426/302 |
| 4,303,452 | 12/1981 | Ohira et al. | 127/32 |
| 4,305,971 | 12/1981 | Stone, Jr. | 426/653 |
| 4,588,600 | 5/1986 | Suderman | 426/555 |
| 4,645,831 | 2/1987 | Lawhon | 530/374 |
| 4,911,942 | 3/1990 | Yajima . | |
| 5,138,038 | 8/1992 | Katayama et al. | 530/343 |
| 5,156,956 | 10/1992 | Motoki et al. | 426/573 |
| 5,308,635 | 5/1994 | Payne et al. | 426/549 |

FOREIGN PATENT DOCUMENTS

| 24297 | 3/1981 | European Pat. Off. . |
| 90559 | 10/1983 | European Pat. Off. . |
| 357 169 | 7/1993 | European Pat. Off. . |
| 372 669 | 10/1993 | European Pat. Off. . |
| 2 156 530 | 6/1973 | France . |
| 49-37270 | 7/1974 | Japan . |
| 02286054 | 2/1991 | Japan . |
| 91/14371 | 10/1991 | Japan . |
| 6105662 | 4/1994 | Japan . |
| 92/15208 | 9/1992 | WIPO . |
| 94/18857 | 9/1994 | WIPO . |

*Primary Examiner*—Lien Tran
*Attorney, Agent, or Firm*—Flynn, Thiel, Boutell & Tanis, P.C.

[57]    ABSTRACT

A food composition comprises gluten, a gliadin or glutenin and food stuff such as (a,c) an additive for chewing gum, (b) a batter for frying, (d,e) a dough, (f) a marine paste and (f) a livestock paste. A food quality such as taste is improved.

3 Claims, No Drawings

CHEWING GUM COMPOSITION CONTAINING GLIADIN AND TRANSGLUTAMINASE this application is a continuation of U.S. Ser. No. 08/342,617, filed Nov. 21, 1994 now abandoned.

FIELD OF INDUSTRIAL APPLICATION

The invention relates to a process for improving the taste and feel of a foodstuff by gliadine, glutenin or a reaction product of a protein with a protein transferase, such as (a) a process for the preparation of an edible chewing gum; (c) a process for the preparation of an edible chewing gum analogue; (b) a batter composition for fried food; (d) a process for manufacturing bread or wheat confectionery; (e) a process for manufacturing bread or wheat confectionery; and (f) a process for producing a seafood or livestock paste product and to a quality improver therefor.

PRIOR ARTS

EP-A 357 169 and EP-A 372 669 disclose the application of gluten and glutenin to oil, fat and vitamins. Gluten is contained in wheat. Glutenin and gliadine can be obtained from wheat gluten. The fractionation of wheat gluten into gliadin and glutenin is conducted as follows: a fraction of gliadin, which is a soluble component prepared by extracting wheat gluten with a 70% aqueous solution of ethanol and freeing the supernatant from the solvent, while a glutenin fraction is prepared by recovering crude glutenin from the extraction mixture as a precipitate and washing the crude glutenin with the same aqueous solution as that used above; and the obtained fractions were each dried and pulverized.

JP-B 49-37270(1974) discloses a process for the preparation of a gum analogue which comprises thermally denaturing wheat gluten to a slight extent to form a gum base. However, this process is characterized by thermally bonding wheat gluten to form a gum base. Therefore, the product prepared by the severe thermal treatment of wheat gluten loses its re-agglomeratability after chewing to result in a hard brittle substance, while that prepared by the slight thermal treatment thereof has an elasticity inherent in chewing gum, but is problematic in that the elasticity lowers by chewing because of the weak bonding of the product to result in a sticky substance.

SUMMARY OF THE INVENTION

The invention provides a food composition comprising gluten, a gliadin or glutenin and a food stuff. The food stuff is selected from the group consisting of (a,c) an additive for chewing gum, (b) a batter for frying, (d,e) a dough, (f) a seafood paste and (f) a livestock paste. It is preferable that the composition comprises a gliadin-rich fraction of wheat gluten or a glutenin-rich fraction of wheat gluten. There are provided as embodiments of the invention: (a) To provide a process for preparing an edible chewing gum having such an elasticity and an extensibility as to give comfort similar to that of the chewing gum of the prior art in chewing, without using any synthetic high-molecular substance. The above process is characterized by using, as the gum base, a substance prepared by thermally treating the gliadin-rich fraction of wheat gluten in a water-containing state in a pH range of 4 to 11 to denature the gliadin; (c) To provide a process for preparing an edible chewing gum analogue which is highly safe and has such an elasticity as to give a comfort similar to that of chewing gum during chewing without using any chemically synthesized material. The above process comprises mixing an animal or vegetable protein such as wheat gluten or the gliadin fraction thereof with a protein transferase to crosslink the protein by the action of the enzyme through the linkage between amino residues; (b) To provide a batter composition for fried food, which barely exhibits viscosity change due to stirring or temperature rise, has a proper ability to form gluten, and can give a coating which has excellent crispiness and changes little with the lapse of time. The above batter composition can be prepared by incorporating the glutenin-rich fraction prepared by extracting wheat gluten with an aqueous solution of ethanol into batter for fried food in a concentration of 0.5% by weight or above (in terms of glutenin); (d) To improve the water absorption of glutenin to thereby provide a process for manufacturing bread or wheat confectionery having excellent expansion. The above process is characterized by using a dough composition comprising 100 parts by weight of wheat flour and at least 0.5 part by weight of a glutenin-rich fraction prepared by extracting wheat gluten with an acidic aqueous solution of ethanol having a concentration of 30% by volume or below; (e) To provide a process for manufacturing bread or wheat confectionery which is prevented from aging and being denatured during freezing. The above process is characterized by using a dough composition comprising 100 parts by weight of wheat flour and at least 0.5 part by weight of a gliadin-rich fraction prepared by extracting wheat gluten with an acidic aqueous solution of ethanol having a concentration of 30% by volume or below; (f) To provide a process for producing a seafood or livestock paste product in which the springiness, especially the rupture elongation is not lost, even by heat treatment at high temperatures, and further provide a quality improver for use in the above process. A process for producing a seafood or livestock paste product, comprising incorporating a fraction composed mainly of gliadin, which has been extracted from wheat gluten with a lower alcohol, and whose gliadin content is at least 50% by weight, in a raw meat in an amount of at least 0.2% by weight based on the raw meat, and a quality improver comprising the above fraction as the active ingredient.

DETAILED DESCRIPTION OF THE INVENTION

The food composition (a) comprises, as the gum base, a substance prepared by thermally treating the gliadin-rich fraction of wheat gluten in a water-containing state in a pH range of 4 to 11 and an additive for chewing gum.

The food composition (c) comprises, as a chewing gum analogue, a product obtained by mixing a gliadin-rich fraction of wheat gluten or a wheat gluten with a protein transferase to crosslink the protein(s) through linking amino residues.

The food composition (b) comprises a glutenin-rich fraction of wheat gluten and a batter.

The composition (d) comprises 100 parts by weight of wheat flour and/or starch flour as a dough for bread or wheat confectionery and at least 0.5 part by weight of a glutenin-rich fraction prepared by extracting wheat gluten with an acidic aqueous solution of ethanol having a concentration of 30% by volume or below.

The composition (e) comprises 100 parts by weight of wheat flour and/or starch flour as a dough for bread or wheat confectionery and at least 0.5 part by weight of a gliadin-rich fraction prepared by extracting wheat gluten with an acidic aqueous solution of ethanol having a concentration of 30% by volume or below.

The composition (f) comprises a seafood or livestock paste product and a fraction composed mainly of gliadin which has been separated from wheat gluten.

It is preferable that said fraction composed mainly of gliadin contains gliadin in an amount of at least 50% by weight.

The invention provides the use of gliadin or glutenin or gluten as an additive to a food stuff to improve its taste and quality.

This invention provides application of gliadin or glutenin to a food stuff such as chewing gum, an analogous product of chewing gum, a batter for frying, dough, bread, wheat confectionary, marine paste, livestock paste to improve the taste or feel of the food and improve performance of the food. The taste-improver of the invention includes (a) a product obtained or obtainable by heating a fraction of gliadin which is adjusted to include water therein and have a pH value of 4 to 11, (c) a product obtained or obtainable by reacting a fraction of gliadin with a protein transferase to crosslink the amino groups of gliadin, (b),(f) a fractionated product of gliadin, (d) glutenin obtained or obtainable by extracting gluten with an acidic, aqueous ethanol solution including 30 percent by volume or less of ethanol, (e) gliadin obtained or obtainable by extracting gluten with an acidic, aqueous ethanol solution including 30 percent by volume or less of ethanol. As gliadin and gluten, a fractionation product that is rich in either one may be practically used.

The taste-improver or food quality-improver of the invention includes (a) a product obtained or obtainable by heating a fraction of gliadin which is adjusted to include water therein and have a pH value of 4 to 11, (c) a product obtained or obtainable by reacting a fraction of gliadin with a protein transferase to crosslink the amino groups of gliadin, (b),(f) a fractionated product of gliadin, (d) glutenin obtained or obtainable by extracting gluten with an acidic, aqueous ethanol solution including 30 percent by volume or less of ethanol, (e) gliadin obtained or obtainable by extracting gluten with an acidic, aqueous ethanol solution including 30 percent by volume or less of ethanol.

As gliadin and gluten, a fractionation product that is rich in either one may be practically used.

DETAILED DESCRIPTION OF EMBODIMENTS OF THE INVENTION (a) The present invention aims at providing a process for preparing an edible chewing gum having such an elasticity and an extensibility as to give comfort similar to that of the chewing gum of the prior art in chewing without using any synthetic high-molecular substance.

The inventors of the present invention have found that a substance having extensibility and elasticity can be prepared by separating gliadin (defined as "substance soluble in 70% ethanol"), which is a globular protein constituting wheat gluten and is a sticky substance, from glutenin, which is a fibrous protein constituting it and is an elastic substance, and partially thermally denaturing the obtained gliadin-rich fraction. The present invention has been accomplished on the basis of this finding.

The chewing gum analogue prepared by the use of wheat gluten according to the above Japanese Patent crumbles after a short-time of chewing to result in a substance far from chewing gum, though it is an elastic gummy substance at the beginning of chewing. Further, when wheat gluten is thermally treated at such a high temperature, the obtained product is not a gum but is hard and rubbery. In contrast thereto, even when wheat gluten is thermally treated at low temperature to control the degree of thermal denaturation, the extensibility of the product is unfaborably in inverse proportion to the hardness thereof, i.e., the attainment of a gumlike elasticity brings about a poor extensibility so far as the composition of the gluten is not changed.

The present invention is characterized by using a gliadin-rich fraction having an enhanced gliadin content as compared with wheat gluten (gliadin content of ordinary active gluten powder: about 33%). The fraction is remarkably inhibited from hardening during thermal treatment to give an elastomer having excellent extensibility.

Namely, the present invention relates to a process for the preparation of a chewing gum, characterized by using, as the gum base, a substance prepared by thermally treating the gliadin-rich fraction of wheat gluten in a water-containing state in a pH range of 4 to 11.

The gliadin-rich fraction can be prepared by extracting wheat gluten with an aqueous solution of ethanol having a concentration of 30 to 70% by volume or an acidic aqueous solution of ethanol having a concentration of 30% by volume or below and fractionating the supernatant obtained by the extraction by the addition of water, drying, pH adjustment, or other means.

The above extraction can be conducted with, e.g., an aqueous solution of ethanol having a concentration of 30 to 70% by volume, an aqueous solution of isopropyl alcohol or n-propanol having a concentration of 10 to 20% by volume, or an aqueous solution of acetone having a concentration of 20 to 50% by volume to give a fraction having a gliadin concentration of as high as 80% or above, and the extraction can also be conducted with an acidic aqueous solution of ethanol having a concentration of 5 to 20% by volume and a pH of 3.5 to 5.5 to give a gliadin fraction having a concentration of as much as 50% or above, though the extractant is not limited to them. The gliadin concentration of the fraction can be controlled by varying the composition of the extractant and/or the extraction conditions. The gliadin-rich fraction to be used in the present invention may be any one containing gliadin in an amount of 50% or above on a dry basis.

The gliadin-rich fraction according to the present invention may be any of wet and dry ones and the dry fraction is wetted prior to the thermal denaturation. It is preferable that the gliadin-rich fraction prepared by water addition or pH adjustment be thermally treated in a wet state containing at least 10% water, while that prepared by drying be thermally treated in a wet or water-containing state containing at least 15% water, though the preferable water content is varied depending upon the subsequent process for the preparation of chewing gum.

The gliadin-rich fraction is thermally treated in a wet or water-containing state. Alternatively, the supernatant obtained by the extraction may be subjected to the thermal treatment. Although the gliadin-rich fraction to be thermally treated must have a pH ranging from 4 to 11, other treatment conditions are not limited, and can be varied widely. For example, the thermal treatment is preferably conducted at a pH ranging from 5 to 8 and a temperature ranging from 55° to 100° C. for 1 to 120 minutes. Although heating methods include direct heating methods using steam and heated air and indirect heating methods, the object of the present invention can be attained by any of them, so that the heating method to be employed in the thermal treatment of the present invention is not limited. Further, a combination of two or more of these heating methods may be employed.

The heating time of the thermal treatment is determined from consideration of the wetness and pH of the fraction to be thermally treated and the temperature of the thermal treatment. In other words, the heating time must be so determined that the object of the treatment does not lose its extensibility or elasticity. For example, a gliadin-rich fraction having a water content of 40 to 80% by weight and a pH of 6.5 to 7.0 is thermally treated under the conditions of 65° C. and 120 minutes, 70° C. and 30 minutes, or 80° C. and 15 minutes, among which the conditions of 70° C. and 30 minutes are preferable.

The thermal treatment can be conducted not only by the method described above but also after the blending of the fraction with other raw materials for chewing gum. The thermal treatment may be conducted at any stage.

Although the process for preparing a chewing gum from the product of the thermal treatment, i.e., gum base is not limited, a chewing gum is preferably prepared by dehydrating the gum base by drying or other means until the water content is lowered to 50% or below, mixing the resulting gum base with a sweetener, a perfume, a dye or the like, kneading the obtained mixture, rolling the resulting mixture into a sheet, and cutting the sheet into proper sizes. If necessary, the sheet may be re-dried or dusted with a powder for the purpose of changing the hardness of the gum or preventing the sticking among pieces of the gum.

The present invention has been accomplished on the basis of the finding that the gliadin-rich fraction of wheat gluten can be converted into a chewing-gum-like substance having extensibility and elasticity through the mild thermal treatment.

(c) The present invention aims at providing a process for preparing an edible chewing gum which is highly safe and has such an elasticity as to give comfort similar to that of the chewing gum of the prior art in chewing, without using any chemically synthesized material.

The inventors of the present invention have found that various animal and vegetable proteins are crosslinked through the linkage between amino residues by treatment with a protein transferase at a strength far higher than that attained by thermal treatment, and that the above object can be attained by utilizing this property of the proteins. The present invention has been accomplished on the basis of these findings.

Namely, the present invention relates to a process for the preparation of a chewing gum analogue, characterized by mixing one or more of animal and vegetable proteins with a protein transferase to crosslink the protein(s) through a linkage between amino residues.

The animal and vegetable proteins to be used in the present invention include vegetable ones such as gluten, gliadin, zein and soybean protein; and animal ones such as casein, gelatin and egg albumin.

The term "gliadin" generally refers to a 70% ethanolic extract of wheat gluten. In the present invention, however, the term is not limited to the extract, but includes paste prepared from the extract and dry powder of the extract prepared by, e.g., spray drying, as far as they contain gliadin. In such a case, it is preferable that the paste or the powder contain at least 50% by weight of gliadin. A dry powder containing 50 to 90% by weight of gliadin is particularly preferable.

The method for preparing an extract having a gliadin concentration of as high as 80% or above includes methods using a 30 to 70% by volume aqueous solution of ethanol, a 10 to 20% by volume aqueous solution of isopropyl alcohol or n-propanol and a 20 to 50% by volume aqueous solution of acetone, respectively, while the method for preparing an extract having a gliadin concentration of as much as 50% by weight or above includes a method using a 5 to 20% by volume acidic aqueous solution of ethanol having a pH of 3.5 to 5.5. The supernatant obtained by the extraction according to the above method is fractionated by the addition of water, drying, pH adjustment, or other means to give a fraction containing at least 50% by weight of gliadin. Such a fraction is referred to as "gliadin-rich fraction" hereinbelow.

The gluten to be used in the present invention may be any one which is separated from wheat and contains gluten in an amount of 50% by weight or above, preferably about 80% by weight or above on a dry basis. Commercially available active gluten powders may be used.

The gluten and gliadin to be used in the present invention may be those which are thermally denatured or reduced.

The protein transferase to be used in the present invention is not particularly limited, but many kinds of protein transferases can be used in the present invention. In particular, it is preferable to use transglutaminase which catalyzes the acyl-transfer reaction between the γ-carboxamide group of a glutamine residue present in a protein or peptide chain and various primary amines. Transglutaminase is commercially available as a preparation under the trade name of "Activa TG-K" (a product of Ajinomoto Co., Ltd.). This enzyme is known to be one which catalyzes the reaction of forming ε-(γ-Glu)-Lys linkage between the glutamine residue and ε-amino group of lysine residue among the amino acids constituting a protein intramolecularly or intermolecularly.

When the above transglutaminase preparation (Activa TG-K) is used as the protein transferase, the amount thereof may be about 0.05 to 3% by weight based on the protein(s). Generally, the preparation is used in an amount of 0.1 to 1% by weight.

When two or more proteins selected from among animal and vegetable ones are used, the ratio between (or among) them is not limited, but varies depending upon the kinds of the proteins. For example, when gliadin or gluten is combined with casein, it is preferable that the weight ratio of gliadin (or gluten) to casein lie between 20:1 and 2:1.

Among animal and vegetable proteins, one which can form a salt with an alkali metal like casein may be used as such a salt. Although the kind of salt is not limited, the salt is preferably a calcium or sodium salt, still preferably a water-insoluble calcium salt.

The mixing of the above protein(s) with a protein transferase may be conducted by a method which comprises premixing at least one of animal and vegetable protein powders with a powdery protein transferase and adding water to the obtained mixture, or a method which comprises dispersing a powdery protein transferase in water and adding the resulting aqueous dispersion to at least one of animal and vegetable proteins. Thus, the order of addition and the method of mixing are not limited.

For example, it is preferable to employ a method which comprises adding transglutaminase to a mixture comprising an animal or vegetable protein as the gum base, a pH regulator which can attain the optimum pH (6 to 7) for the protein transferase, a perfume, a sweetener, a dye, a polyol such as glycerin or a product resulting from the reduction of sugar and so forth, and adding water to the obtained mixture, or a method which comprises dissolving and dispersing transglutaminase, a pH regulator comprising a water-soluble substance, and so forth in water and mixing the obtained aqueous dispersion with the rest of the components.

The chewing gum analogue of the present invention can be prepared by rolling the mixture prepared above into a belt having a thickness of 1 to 2 mm, keeping the belt at the optimum temperature for the reaction with the protein transferase (about 50° to 55° C. for transglutaminase) for tens of minutes, deactivating the enzyme, removing excess water from the belt and cutting the resulting belt into proper sizes.

Alternatively, the chewing gum analogue can also be prepared by adding an aqueous dispersion containing both a pH regulator and a protein transferase to at least one of animal and vegetable proteins, making the obtained mixture react at an optimum temperature for the enzyme to form a gum base, adding a perfume, a sweetener, a sour-tasting material, a dye, a polyol, and so forth to the base, kneading the obtained mixture, and treating the resulting mixture in the same manner as that described above.

According to the process of the present invention, an animal or vegetable protein is crosslinked by the action of a protein transferase through the reaction between amino residues of protein molecules, so that the resulting crosslinked protein exhibits physical properties similar to those of chewing gum and has a tissue which is not softened by chewing. Further, owing to the crosslinking between different kinds of proteins, the obtained gum base of the present invention has the property of losing its agglomeratability after being chewed for a certain time.

(b) The present invention aims at providing a batter composition for fried food which hardly exhibits a viscosity change due to stirring and/or temperature rise, has a proper ability to form gluten, exhibits shape-retaining and volume-increasing effects, and can give a flavorous coating which is excellent in crispiness and hardly changes with the lapse of time.

The inventors of the present invention have found that a batter composition prepared by fractionating wheat gluten into glutenin (substance insoluble in 70% ethanol), which is an elastic component of wheat gluten, and gliadin, which is a viscous component thereof, and mixing wheat flour with the obtained glutenin-rich fraction hardly exhibits a viscosity change and can give a porous coating having excellent vapor permeability by deep-frying. The present invention has been accomplished on the basis of this finding.

Namely, the present invention relates to a batter composition for a fried food, characterized by containing the glutenin-rich fraction of wheat gluten.

A batter composition having a high gliadin content has a problem in that extensible gluten is formed. On the contrary, the use of the glutenin fraction according to the present invention brings about an enhanced glutenin content, which prevents the formation of extensible gluten to enable the preparation of a batter which hardly exhibits a viscosity change due to stirring or the like and can give a brittle coating even when thermally denatured. Further, a batter having an enhanced glutenin content has a proper viscosity even when gluten is formed therein, because the formed gluten is not extensible. Accordingly, the coating made from the batter has excellent crispiness and can retain its excellent palatability for a lengthened time.

The glutenin-rich fraction can be prepared by extracting wheat gluten with a 30 to 70% by volume aqueous solution of ethanol or an acidic aqueous solution of ethanol having a concentration of 30% by volume or below and removing the supernatant from the extraction system to recover an insoluble matter.

The method for preparing the glutenin-rich fraction according to the present invention is not limited at all. For example, the process for preparing a glutenin fraction having a concentration of as high as 80% by weight or above includes a process wherein a 30 to 70% by volume aqueous solution of ethanol is used, wherein a 10 to 20% by volume aqueous solution of isopropyl alcohol or n-propyl alcohol is used, or wherein a 20 to 50% by volume aqueous solution of acetone is used, while the process for preparing a glutenin fraction having a medium concentration (50% by weight or above but less than 80% by weight) includes a process wherein an acidic aqueous solution of ethanol having a pH of 3.5 to 5.5 and a concentration of 5 to 20% by volume is used.

The glutenin concentration of the fraction can be controlled by changing the composition of the solvent or the above conditions. The glutenin-rich fraction according to the present invention may be any one containing glutenin in a concentration of 40% by weight or above on a dry basis or any one containing it in a concentration of 50% by weight or above based on the protein.

The glutenin-rich fraction may be added to batter in the form of the insoluble matter recovered above as such or in the form of a powder prepared by drying the insoluble matter, though the form is not particularly limited. The fraction is preferably added as a dry powder. The method for drying the insoluble matter is preferably spray drying, though it is not limited.

The batter composition of the present invention may contain the glutenin-rich fraction in an amount (in terms of glutenin) of 0.5% by weight or above, based on the weight of the whole composition including water. It is preferable that the fraction be added in an amount of 1 to 30% by weight, still preferably 1 to 15% by weight based on the wheat flour used.

The batter composition of the present invention generally comprises 70 to 100% by weight of wheat flour. Further, the composition can exhibit the effects of the present invention, even when it further contains conventional additives such as common salt, baking powder, egg white powder, dried egg, skim milk powder, shortening, seasoning, starch, raw egg, thickener and/or gelling agent.

The fried food made by the use of the above batter composition includes the above-mentioned batter-fried foods, and the raw material to be coated with the batter composition includes vegetables, fish and shellfish, meat, processed foods and other various materials, though it is not limited to them.

According to the present invention, a wheat flour mixture having an enhanced glutenin content is prepared by adding glutenin, which is a constituent of wheat gluten, to wheat flour; and a batter composition is prepared by the use of this mixture. The thus-obtained batter composition is characterized in that the gluten formed by stirring is nonviscous, and therefore when the batter composition is deep-fried, it gives a porous coating which has a brittle tissue, excellent in crispiness and hardly changes with the lapse of time. Further, glutenin is a constituent of wheat flour, so that the addition thereof to wheat flour does not impair the flavor inherent in the coating.

(d) The present invention aims at providing a process for manufacturing bread or confectionery having excellent expansion, characterized by using glutenin having improved water absorption as a component of dough for bread or confectionery to utilize the high ability of the glutenin to retain carbon dioxide. Further, the present invention also aims at providing a process for manufacturing bread or confectionery containing a reduced amount of gliadin, which is believed to be an allergen.

The inventors of the present invention have found that a glutenin fraction having excellent water absorption and miscibility can be obtained by extracting wheat gluten with an acidic aqueous solution of ethanol having a low concentration and that when this fraction is added to dough for bread or confectionery, the glutenin is rapidly bonded to the lipid contained in the dough to form an enhanced amount of an impermeable thin membrane having an ability to retain carbon dioxide, which makes it possible to manufacture bread or confectionery of enhanced expansion. The present invention has been accomplished on the basis of these findings. Further, they have also found that the use of an emulsifying agent with the glutenin fraction can further enhance the above effects to accomplish the present invention.

Namely the present invention provides a process for manufacturing bread or wheat confectionery, characterized by using a dough composition comprising 100 parts by weight of wheat flour and/or starch flour and at least 0.5 part by weight (on dry basis) of a glutenin-rich fraction prepared by extracting wheat gluten with an acidic aqueous solution of ethanol having a concentration of 30% by volume or below.

The acidic aqueous solution of ethanol having a concentration of 30% by volume or below may be one prepared by adding at least one compound selected from the group consisting of acetic, citric, malic, lactic, adipic, fumaric, tartaric and gluconic acids, glucono-δ-lactone, phosphoric and phytic acids, and salts thereof with calcium, potassium and sodium, to an aqueous solution of ethanol having a concentration of 30% by volume or below, preferably 5 to 30% by volume, still preferably 10 to 20% by volume to acidify the solution. It is preferable that the acidic aqueous solution exhibit a pH of 5.5 to 3.0 when wheat gluten is dispersed therein.

The glutenin-rich fraction (hereinafter sometimes abbreviated to "the glutenin fraction") can be prepared by, e.g., a process which comprises dispersing 1 to 1.5 kg of activated gluten powder in 10 l of an acidic aqueous solution of ethanol prepared by dissolving 0.2% by weight of citric acid in a 10% by volume aqueous solution of ethanol, stirring the obtained dispersion at room temperature for 2 hours to conduct extraction, centrifuging the extraction mixture to recover a formed precipitate, adding 1 to 3 times as much water to the precipitate, and spray-drying the obtained dispersion.

The precipitate prepared above from wheat gluten contains 10 to 70% by weight (on a dry basis) of glutenin and can be used as such in the present invention as the glutenin-rich fraction. It is preferable that glutenin account for at least 50% by weight of the protein contained in the precipitate. Alternatively, the glutenin-rich fraction may be added to the wheat flour to be used in the preparation of dough for bread or confectionery as a paste or dry powder prepared from the above extract, though the addition thereof as a dry powder is preferable.

Generally, the water absorption, miscibility and other properties of powdery gliadin or glutenin vary depending upon the kind of the solvent used in the extraction of wheat gluten, the method of removing the solvent and the method of pulverization, and these properties of powdery gliadin and powdery gluten greatly affect the water absorption rate in the formation of gluten, gluten-forming time and the properties of dough. The glutenin-rich precipitate obtained by the extraction of wheat gluten with an acidic aqueous solution of ethanol having a low concentration according to the present invention has superior water absorption and miscibility as compared with the glutenin prepared by the extraction thereof with an aqueous solution of ethanol having a high concentration. Further, when the precipitate is added to dough, it is rapidly bonded to a lipid contained in the dough to form an enhanced amount of an impermeable thin membrane having an ability to retain carbon dioxide, thus enabling the manufacturing of bread or wheat confectionery having excellent expansion.

The method of adding the glutenin fraction to dough for bread includes one which comprises premixing wheat flour or other powdery material with the glutenin fraction as dry powder, and one which comprises adding the glutenin fraction as a paste in some stage in the course of the preparation of dough. Though the method is not limited to them, the method of adding it to a powdery material is preferable, and the addition thereof to wheat flour is still preferable.

The time of addition of the glutenin fraction is not limited. In manufacturing bread according to the direct dough process, the fraction is preferably added to the starting wheat flour, while in manufacturing it according to the sponge-dough process, the fraction is preferably added to the wheat flour in the sponge or the wheat flour as the main component. In manufacturing wheat confectionery, the fraction may be added to a powdery raw material such as a powder mix, or wheat flour.

The amount of the glutenin fraction to be added may be 0.5% by weight or above, preferably 0.5 to 5.0% by weight based on the wheat flour used as the raw material on dry basis. When bread or confectionery containing allergens in a reduced amount is made without wheat flour, the amount of the fraction may be 3% by weight or above based on the starch flour used, with 10 to 20% by weight being preferable for bread, while 4 to 15% by weight for confectionery.

It is a matter of course that ordinary additives for bread and confectionery can be used in the manufacturing of bread and wheat confectionery according to the present invention. Such additives include emulsifying agents, natural gums, antibacterial agents, pH regulators, souring agents, seasonings, sweeteners, expanding agents, dyes, processed starches, and emulsified oils and fats. In particular, when an emulsifying agent is additionally used, bread or confectionery having enhanced expansion can be made even by the use of a pretty small amount of the glutenin fraction.

The emulsifying agent usable in the present invention includes glycerol fatty acid esters, sucrose fatty acid esters, sorbitan fatty acid esters, propylene glycol fatty acid esters, polyoxyethylene emulsifying agents, calcium stearoyllactate, sodium stearoyllactate, lecithin and enzyme-treated lecithin. The glycerol fatty acid esters include monoglycerides with organic acids such as lactic, tartaric and succinic acids; and esters of polyglycerol (condensate of glycerol) with fatty acids.

When an emulsifying agent is used simultaneously with the glutenin fraction, the emulsifying agent may be mixed with the glutenin fraction in powdery form or the emulsifying agent and the fraction may be separately added to dough for bread. The mixing of an emulsifying agent with the glutenin fraction in powdery form is preferable. Alternatively, it is possible to employ a process which comprises dissolving or dispersing an emulsifying agent in the dispersion of the precipitate comprising the glutenin fraction before drying, and powdering the resulting mixture. The amount of the emulsifying agent added is preferably 1 to 100% by weight based on the glutenin fraction.

The bread according to the present invention includes bread, hard baked roll, sweet roll, doughnut, steamed roll, English muffin and bagel, while the wheat confectionery is roughly classified into Japanese-style confectionery and Western-style confectionery. The former includes steamed cakes, baked cakes and baked dry confectioneries, while the latter includes sponge cakes, batter cakes, choux, yeast pastries, flaky pastries and biscuits.

(e) The present invention aims at providing a process for manufacturing bread or wheat confectionery which is prevented from aging for a long time and has excellent expansibility, characterized by using gliadin having improved water absorption as a component of the dough for bread or confectionery. Further, the present invention also aims at providing a process for manufacturing frozen dough bread, frozen baked bread or frozen confectionery which hardly denatures during freezing.

The inventors of the present invention have found that a gliadin fraction having excellent water absorption and miscibility can be obtained by extracting wheat gluten with an acidic aqueous solution of ethanol having a low concentration and that, unlike dough prepared by the addition of gluten, dough prepared by the addition of this gliadin fraction is baked to give a product which is prevented from aging and denaturing during freezing, without being accompanied with any increase in the hardness, i.e., with the original softness being maintained. The present invention has been accomplished on the basis of this finding. Further, they have also found that the use of the gliadin fraction with an emulsifying agent and/or a pH regulator can further enhance the above effects to accomplish the present invention.

Namely, the present invention provides a process for manufacturing bread or wheat confectionery, characterized by using a dough composition comprising 100 parts by weight of wheat flour and/or starch flour and at least 0.5 part by weight (on dry basis) of a gliadin-rich fraction prepared by extracting wheat gluten with an acidic aqueous solution of ethanol having a concentration of 30% by volume or below.

The acidic aqueous solution of ethanol having a concentration of 30% by volume or below may be one prepared by adding at least one compound selected from the group consisting of acetic, citric, malic, lactic, adipic, fumaric, tartaric and gluconic acids, glucono-δ-lactone, phosphoric and phytic acids, and salts thereof with calcium, potassium and sodium, to an aqueous solution of ethanol having a concentration of 30% by volume or below, preferably 5 to 30% by volume, still preferably 10 to 20% by volume to acidify the solution. It is preferable that the acidic aqueous solution exhibit a pH of 5.5 to 3.0 when wheat gluten is dispersed therein.

The gliadin-rich fraction (hereinafter sometimes abbreviated to "the gliadin fraction") can be prepared by, e.g., a process which comprises dispersing 1 to 1.5 kg of activated gluten powder in 10 l of an acidic aqueous solution of ethanol prepared by dissolving 0.2% by weight of citric acid in a 10% by volume aqueous solution of ethanol, stirring the obtained dispersion at room temperature for 2 hours to conduct extraction, centrifuging the extraction mixture to recover a supernatant and, if necessary, concentrating and spray-drying the supernatant.

The dry powder thus separated from wheat gluten contains gliadin in an amount of at least 50% by weight, preferably 65 to 90% by weight on a dry basis and can be used as such in the present invention as the gliadin-rich fraction. Further, a pasty gliadin fraction prepared by precipitating gliadin from the above extract by pH adjustment and recovering the precipitate may also be used in the present invention, though the above dry powder is preferably used.

Generally, the water absorption, miscibility and other properties of powdery gliadin extremely varies depending upon the kind of the solvent used in the extraction of wheat gluten, the method of removing the solvent and the method of pulverization, and these properties of powdery gliadin greatly affect the water absorption rate in the formation of gluten, gluten-forming time and the properties of dough. The extraction of wheat gluten with an acidic aqueous solution of ethanol having a low concentration according to the present invention can give a gliadin fraction having superior excellent water absorption and miscibility compared to one obtained by the extraction thereof with an aqueous solution of ethanol having a high concentration. Further, this gliadin fraction can be easily added to dough for bread or confectionery and can enhance the expansibility of the dough. Furthermore, the gliadin fraction is effective in preventing dough from denaturing during freezing, makes it possible to manufacture a baked wheat food without any increase in the hardness, and serves to prevent the baked wheat food from aging.

The method of adding the gliadin fraction to dough for bread or confectionery includes one which comprises premixing wheat flour or another powdery material with the gliadin fraction as dry powder, one which comprises dispersing the gliadin fraction in part or the whole of the water to be mixed, emulsifying an oil or fat in the obtained dispersion to form an emulsion curd, and adding this emulsion curd to the rest of the water to be mixed or wheat flour, and one which comprises adding the gliadin fraction as a paste at some stage in the course of the preparation of dough. Though the method is not limited to them, the method of adding it to a powdery material is preferable, and the addition thereof to wheat flour is still preferable.

The time of addition of the gliadin fraction is not limited. In manufacturing bread according to the direct dough process, the fraction is preferably added to the starting wheat flour, while in manufacturing it according to the sponge-dough process, the fraction is preferably added to the wheat flour in the sponge or the wheat flour as the main component. In manufacturing wheat confectionery, the fraction may be added to powdery raw material such as powder mix, or wheat or starch flour.

The amount of the gliadin fraction to be added may be 0.5% by weight or above, preferably 0.5 to 20.0% by weight, based on the wheat flour used as the raw material, on a dry basis. When bread or confectionery is made without wheat flour, the amount of the fraction may be 3% by weight or above, based on the starch flour used, with 10 to 30% by weight being preferable for bread, while 5 to 20% by weight for confectionery.

It is a matter of course that ordinary additives for bread and confectionery can be used in the manufacture of bread and wheat confectionery according to the present invention. Such additives include emulsifying agents, natural gums, antibacterial agents, pH regulators, souring agents, seasonings, sweeteners, expanding agents, dyes, processed starches, emulsified oils and fats, oligosaccharides, reduced saccharides, and peptides. In particular, when an emulsifying agent, pH regulator, natural gum and/or processed starch is additionally used, bread or confectionery which is prevented from aging and denaturing during freezing can be made, even through the use of a pretty small amount of the gliadin fraction.

The emulsifying agent usable in the present invention includes glycerol fatty acid esters, sucrose fatty acid esters, sorbitan fatty acid esters, propylene glycol fatty acid esters, polyoxyethylene emulsifying agents, calcium stearoyllactate, sodium stearoyllactate, lecithin and enzyme-treated lecithin. The glycerol fatty acid esters include monoglycerides with organic acids such as lactic, tartaric and succinic acids; and esters of polyglycerol (condensate of glycerol) with fatty acids.

When an emulsifying agent is used simultaneously with the gliadin fraction, the emulsifying agent may be mixed with the gliadin fraction in powdery form or the emulsifying agent and the fraction may be separately added to powdery material for bread or confectionery or dough therefor. The mixing of an emulsifying agent with the fraction is preferable. Alternatively, it is possible to employ a process which comprises dissolving or dispersing an emulsifying agent in the supernatant formed by the extraction of wheat gluten, and powdering the resulting mixture. The amount of the emulsifying agent added is preferably 1 to 100% by weight based on the gliadin fraction.

The pH regulator usable in the present invention includes adipic, citric and gluconic acids, glucono-δ-lactone, succinic, acetic, tartaric, lactic, fumaric, malic, carbonic and phosphoric acids, and salts thereof with potassium, sodium and calcium. The amount of the pH regulator to be added is preferably 0.1 to 10% by weight based on the gliadin fraction. The pH regulator may be added in a similar manner to the above mentioned manner for adding an emulsifying agent.

The natural gum includes alginic acid, its sodium salt, gum arabic, curdlan, carob bean gum, xanthan gum, chitin, chitosan, guar gum, psyllium seed gum, carrageenan, tamarind seed gum, tragacanth gum, pectin, gellan gum and gelatin. The amount of the gum to be added is preferably 0.01 to 10% by weight based on the wheat flour, and the gum is preferably mixed with the gliadin fraction or other powdery material.

The bread according to the present invention includes bread, hard baked roll, sweet roll, doughnut, steamed roll, English muffin, bagel and bread for bread crumbs, while the wheat confectionery is roughly classified into Japanese-style confectionery and Western-style confectionery. The former includes steamed cakes and baked cakes, while the latter includes sponge cakes, batter cakes, choux, yeast pastries and flaky pastries.

(f) It is an object of the present invention to provide a process for producing a seafood or livestock paste product having an ameliorated quality, especially ensuring an increase of the rupture elongation not only in the formation of springiness during standing but also in the heat treatment at high temperatures, and it is another object of the present invention to provide a quality ameliorant for use to attain the above object.

The present invention provides a process for producing a seafood or livestock paste product, characterized by incorporating a fraction composed mainly of gliadin which has been separated from wheat gluten in a seafood or livestock paste product, and also provides a quality improver containing the above fraction.

In the present invention, the term "fraction composed mainly of gliadin" refers to a fraction obtained by extracting wheat gluten with a lower alcohol. The incorporation of this fraction into the paste product realizes increases of not only the rupture load but also the rupture elongation which have never been attained by the use of other proteins, and prevents the loss of the above properties by the heat treatment at high temperatures. The term "mainly" used herein means "at least 50% by weight of the fraction".

In the fractionation of gliadin from wheat gluten, a fraction having a high content of gliadin (exceeding 80% by weight) may be collected by a method comprising extraction with an aqueous solution containing ethanol in a concentration as high as 50 to 70% by volume. Also, the extraction may be performed by the use of an aqueous solution of isopropanol or n-propanol, in which the propanol concentration is generally in the range of 10 to 20% by volume. Besides alcohols, for example, acetone may also be used in the extraction, which is generally employed as a 20 to 50% by volume aqueous solution.

A fraction containing gliadin in a medium concentration of 50 to 80% by weight may be collected by extracting wheat gluten with an acid aqueous solution containing ethanol in a low concentration. In this collection method, a fraction containing gliadin in a concentration of at least 50% by weight can be obtained by performing the extraction with the use of a 5 to 20% by volume aqueous ethanol solution having a pH value adjusted to 3.5–5.5 by the addition of an organic acid such as lactic, citric, malic or acetic acid or a salt thereof. The gliadin fraction obtained by this collection method is superior in hydratability to the gliadin fraction obtained by the above extraction using the aqueous solution containing ethanol in a high concentration, and its processability is satisfactory.

Although the morphology of the fraction composed mainly of gliadin for use in the present invention is not particularly limited, it is preferred that the fraction be dry powder, thereby ensuring desirable preservability, transportability and workability. Although the method for obtaining dry powder is not particularly limited, it is preferred that the spray drying technique be employed.

The above fraction composed mainly of gliadin may be incorporated in a seafood or livestock paste product by various methods including and not limited to the premix method in which the fraction is mixed with a powdery auxiliary material such as powdery seasoning and additive starch and then the mixture is added to ground seafood or livestock meat, the dissolution dispersion technique in which the fraction is dissolved or dispersed in a liquid auxiliary material such as liquid seasoning, pickle and additive water and then added to ground meat, and the method in which the fraction is directly added to seafood or livestock meat at the time of grinding thereof. Of these, the premix method and the dissolution dispersion method are preferred.

When the amount of the added fraction composed mainly of gliadin is at least 0.2% by weight based on the raw meat, the desired effect can be exerted. The amount is preferably in the range of 1 to 5% by weight.

In the process for producing a seafood or livestock paste product according to the present invention, at least one animal or vegetable protein selected from among egg white, milk albumin, serum albumin, casein, gelatin, collagen, wheat gluten and soybean protein, which are conventionally used as springiness enhancers, may be incorporated in the raw meat in addition to the above fraction composed mainly of gliadin.

Further addition to the raw meat of a natural thickening polysaccharide such as agar, curdlan, carrageenan, pectin, konjak (devil's tongue), tamarind gum, gellan gum, xanthan gum, guar gum and locust bean gum is effective in increasing the rupture elongation of the paste product and in providing the paste product with shape retention and syneresis prevention functions.

The incorporation of an emulsifier such as a fatty acid ester of glycerol, a fatty acid ester of sucrose, a fatty acid ester of sorbitan and lecithin in combination with the above components is effective in not only increasing the rupture elongation of the paste product but also in providing other functions such as whiteness improvement.

In the production of kamaboko (shaped and boiled fish meat paste), the addition of a fat or oil increases the rupture elongation of the paste product without lowering the rupture load. The addition of an emulsified fat or oil to ham ensures an improved emulsification stability of the fat or oil and provides the paste product with springiness.

Moreover, the addition of an organic acid such as citric, lactic, malic, fumaric, adipic, tartaric, ascorbic, erythorbic, sorbic, kojic or phytic acid, an inorganic acid such as phosphoric or carbonic acid, and/or sodium, potassium, calcium and magnesium salts thereof improves the preservability of the paste product.

That is, the seafood or livestock paste product is putrescible, and sorbic acid is an approved food preservative therefor. Sorbic acid scarcely exhibits any putrefaction preventing activity in a neutral pH zone, and the lower the pH value, the greater the effect of sorbic acid. Therefore, in the production of seafood or livestock paste products, sorbic acid is often added after lowering the pH of the meat with the use of an organic acid, etc. On the other hand, from the viewpoint of the quality of the obtained product, it is preferred that the pH value in the production steps be adjusted to fall in a neutral zone prior to heat treatment. With respect to the seafood paste product, this pH value is generally in the range of 6.8 to 7.5. Meanwhile, with respect to the livestock paste product, the pH value is generally in the range of 6.0 to 7.0. When the pH adjustment is effected to a zone of values lower than the above range, the resultant product suffers from grave quality deterioration during heat treatment, thereby exhibiting gravely lowered springiness, as compared with that of the product obtained in the neutral pH zone.

When the fraction composed mainly of gliadin for use in the present invention is added to the above paste product, the springiness does not deteriorate, even if the pH value in the production steps is lowered with the use of an organic acid, etc., and even if the heat treatment is conducted at high temperatures in the production steps, so that a product having a high quality and improved preservability can be formed. The feature that the springiness does not deteriorate irrespective of the lowering of the pH value is the major characteristic of the fraction composed mainly of gliadin, which is not exhibited by any of egg white, milk albumin, serum albumin, wheat gluten, soybean protein, etc.

The addition of enzymes such as transglutaminase increases the rupture elongation and shortens the "sitting" time.

Complex combinations of the above additives can impart various functions to the paste product. Further, pharmaceutical preparations can be prepared by such additive combinations. Although the proportions of component additives in each of the preparations are not particularly limited, it is preferred that the above proportions be such that the content of the fraction composed mainly of gliadin is at least 10% by weight.

The seafood paste product to which the present invention applies is, for example, kamaboko (shaped and boiled fish meat paste), fried kamaboko, chikuwa (ring-shaped and boiled fish meat paste) or fish meat sausage. The livestock paste product to which the present invention applies is, for example, ham, sausage, fried pork, boiled pork, hamburger steak or meat ball. These, however, never limit the scope of the paste products to which the present invention applies.

The productive process of the present invention utilizes the properties of the fraction composed mainly of gliadin as a component of wheat gluten, by which the rupture load and the rupture elongation are increased and by which the rupture elongation is not lost, even upon heat treatment. Further, the properties of the fraction by which the rupture load and the rupture elongation are maintained, even in a low pH zone, are utilized in the present invention.

The invention provides some technological advantages: (a) An edible chewing gum having feelings in eating equivalent to those of the chewing gum of the prior art and exhibiting extensibility and elasticity can be prepared by using a gliadin-rich fraction as the gum base; (c) An animal or vegetable protein treated with a protein transferase is used as the gum base, by which it has become possible to provide an edible chewing gum analogue which exhibits feelings similar to those of ordinary chewing gum in eating and which are divided into grains similar to those of rice with the lapse of chewing time to become easy to eat; (b) the glutenin-rich fraction of wheat gluten is used in the preparation of batter for fried food. The batter composition thus prepared is stable in the continuous battering operation conducted in the mass-production of fried food and can give fried food which has excellent crispiness and can retain its initial palatability for a long time; (d) Bread or wheat confectionery having excellent expansion can be manufactured by using a fraction rich in glutenin, which is a constituent of wheat gluten as a component of dough for bread or confectionery, to utilize the property of glutenin of being rapidly bonded to the lipid contained in the dough to form an enhanced amount of an impermeable thin membrane having an ability to retain carbon dioxide; (e) a gliadin-rich fraction prepared by extracting wheat gluten with an acidic aqueous solution of ethanol having a low concentration is added to dough for bread or wheat confectionery to form a dough having a total protein content enhanced by gliadin which is a component constituting wheat gluten and has a quality similar to that of wheat protein; and the use of such a dough makes it possible to manufacture bread or wheat confectionery which is soft and is prevented from aging and denaturing during freezing without impairing the flavor inherent in bread or wheat confectionery and (f) A paste product ensuring an excellent palatability without detriment to the springiness, especially the rupture elongation, even after heat treatment at high temperatures can be obtained by the present invention in which the fraction composed mainly of gliadin is incorporated in a seafood or livestock paste product.

EXAMPLE

The present invention will now be described in more detail by referring to the following Examples. In the Examples, all percentages are by weight, unless otherwise noted.

Example a1 and Comparative Example a1

Wheat gluten (active gluten powder, 1 kg) was dissolved and dispersed in 8 l of a 70% by volume aqueous solution of ethanol. The resulting mixture was agitated with propellers at room temperature for 2 hours to conduct extraction.

The obtained extract was centrifuged to recover a supernatant. This supernatant was concentrated to one fifth of the initial volume, followed by the addition of 10 l of water. Thus, about 800 g of a wet gliadin-rich fraction was obtained. This fraction was put in a vinyl bag and thermally treated at 70° C. for 30 minutes. The resulting fraction was dried until the water content was lowered to 30%. 100 g of the gum base thus prepared was mixed with 100 g of sugar and a small amount of a perfume. The obtained mixture was sufficiently kneaded and rolled into a sheet having a thickness of 1.5 mm. This sheet was cut into pieces having a width of 2 cm and a length of 7 cm. These pieces were dusted with starch and the resulting pieces were stored in a refrigerator at 5° C. for 24 hours to harden them. Thus, a chewing-gum-like product was obtained.

The same active gluten powder as that used above was wetted with thrice as much water and the resulting wet gluten was thermally treated at 65° C. for 30 minutes and thereafter freeze-dried to give dry denatured gluten. 40 g of water-containing glycerin (water content: 33.3%) and a small amount of a perfume were added to a mixture comprising 100 g of the above dry denatured gluten and 100 g of powdered sugar. The obtained mixture was kneaded, rolled and treated in a similar manner to that of Example a1 to give chewing-gum-like products (Comparative Example a1)

These chewing-gum-like products were evaluated by chewing. The products of Example a1 had an excellent feel, accompanied with extensibility and elasticity in eating, even after 10-minute chewing, while those of Comparative Example a1 became brittle after about one minute.

Example a2

In a similar manner to that of Example a1, 1 kg of wheat gluten (active gluten powder) was extracted with an acid aqueous solution of ethanol prepared by dissolving 1.5 g of citric acid in 10 of a 15% by volume aqueous solution of ethanol. The obtained supernatant was concentrated in a vacuum evaporator until the solid concentration of the supernatant reached 10 to 20%. The concentrate was spray-dried to give 350 g of a gliadin-rich fraction as a powder.

150 g of a 0.6% aqueous solution of sodium carbonate was added to 100 g of the fraction prepared above to form a wet gliadin-rich fraction having a pH of 6.8. This wet fraction was put in a container, thermally treated in a water bath at 65° C. for 60 minutes, and thereafter dehydrated in a similar manner to that of Example a1. Sugar and a perfume were added to the resulting fraction at the same proportions as those of Example a1 and the obtained mixture was rolled into a sheet having a water content of 35%. This sheet was dried with hot air at 50° C. for 20 minutes to lower the water content to about 20%. In a similar manner to that of Example a1, the resulting sheet was cut and hardened to give chewing-gum-like products.

These products were evaluated in a similar manner to that of Example a1. Even after 12-minute chewing, they had an excellent feel accompanied with extensibility and elasticity equivalent to those of chewing gum.

Example a3 and Comparative Example a2

The supernatant prepared in Example a2 was adjusted to pH 6.8 and thereafter thermally treated at 65° C. for 30 minutes. The resulting solution was spray-dried, while it was dispersed in a homomixer. Thus, a thermally denatured fraction was obtained. In a similar manner to that of Comparative Example a1, 40 g of water-containing glycerin and a small amount of a perfume were added to a mixture comprising 100 g of the above denatured fraction and 100 g of powdered sugar, and chewing-gum-like products were experimentally prepared from the mixture thus prepared (Example a3).

Further, chewing-gum-like products were prepared in the same manner as that of Comparative Example 1

(Comparative Example a2).

These chewing-gum-like products were evaluated in the same manner as that of Example a1. The products of Example a3 retained their extensibility and elasticity as well as those of Example a1 without crumbling, even after long-time chewing, unlike the products of Comparative Example a2, thus exhibiting excellent properties.

Example a4

100 g of a 0.6% aqueous solution of sodium carbonate was added to 100 g of the gliadin-rich fraction prepared in Example a2 experimentally. The obtained mixture was sufficiently kneaded, followed by the addition of 100 g of sugar, a small amount of a perfume and 25 g of glycerin. The obtained mixture was further kneaded and rolled into a sheet. This sheet was steamed for 5 minutes and freed from the water present on the surface by drying. The resulting sheet was cut and the obtained pieces were treated in the same manner as that of Example a1. Thus, chewing-gum-like products were obtained. The products were evaluated in the same manner as that of Example a1. The products were excellent like those of Example a1.

Referential Example c1

Wheat gluten (active gluten powder, 1 kg) was extracted under stirring with an acidic aqueous solution of ethanol prepared by dissolving 2 g of citric acid in 10 l of a 10% by volume aqueous solution of ethanol. The extract was recovered and the supernatant of the extract was concentrated in a vacuum evaporator until the solid content reached 10 to 20%. The obtained concentrate was spray-dried to give 350 g of a gliadin-rich fraction as a powder. This fraction contained gliadin in an amount of 70%.

Example c1 and Comparative Example c1

0.2 g of a transglutaminase preparation was added to 200 g of the gliadin-rich fraction prepared in the Referential Example c1. The transglutaminase preparation used therein is "Activa TG-K" (a product of Ajinomoto, Co., Ltd.). The obtained mixture was sufficiently agitated, followed by the addition of 100 g of water having the pH adjusted to 6.5 with citric acid and sodium citrate. The obtained mixture was sufficiently kneaded and rolled into a sheet having a thickness of 1.5 mm. This sheet was enclosed in a vinyl bag to avoid being dried, and kept at 50° C. for 30 minutes. The resulting sheet was exposed to steam to deactivate the enzyme. Thereafter, the sheet was cut into sizes equivalent to those of a commercially available chewing gum. Thus, a chewing gum analogue was obtained. Separately, a chewing gum analogue was prepared from the same wheat gluten as that used in the Referential Example c1 according to the process described in JP-B 49-37270/1974 (Comparative Example c1).

The chewing gum analogues prepared above were organoleptically evaluated. The analogue of the Example c1 did not drip, even after 10 minutes of chewing, though that of the Comparative Example c1 began to drip after 2 minutes of chewing.

Example c2

70 g of active gluten powder was mixed with 30 g of pulverized casein, followed by the addition of a dispersion prepared by dissolving and dispersing 0.15 g of a transglutaminase preparation in 100 g of water with its pH adjusted to 6. The obtained mixture was kneaded and rolled into a sheet having a thickness of 1.5 mm. In a similar manner to that of Example c1, the sheet was kept in a thermostat for one hour; the enzyme was deactivated; and the resulting sheet was cut. Thus, a chewing gum analogue was obtained.

This chewing gum analogue was organoleptically evaluated. The chewing gum analogue of this Example had an elasticity higher than that of Example c1. Further, even after 30 minutes of chewing, it neither softened nor became sticky.

Example c3

80 g of the gliadin-rich fraction prepared in Referential Example c1 was mixed with 20 g of calcium caseinate and 0.5 g of a transglutaminase preparation, followed by the addition of 60 g of water with its pH adjusted to 7. The obtained mixture was kneaded, immersed at a temperature of 55° C. for 10 minutes, and thereafter exposed to steam to deactivate the enzyme. Part of the resulting mixture was rolled into a sheet having a thickness of 2 mm and dried until the water content was reduced to 20%. The dried sheet was cut to give a chewing gum analogue.

This chewing gum analogue was organoleptically evaluated. After 5 minutes of chewing, the analogue lost its agglomeratability to result in ricelike grains having an elasticity inherent in chewing gum, which are easy to swallow.

Example c4

30 g of sugar, 10 g of glycerin and a perfume and a dye, each in proper amounts, were added to 50 g of the enzyme-treated protein mixture prepared in Example c3. The obtained mixture was kneaded and the enzyme was deactivated. The resulting mixture was rolled into a sheet having a thickness of 2 mm. The sheet was dried until the water content was lowered to 20%. The dried sheet was cut to give a chewing gum analogue. This chewing gum analogue was organoleptically evaluated. The analogue of this Example had tastes similar to those of chewing gum and exhibited feelings similar to those thereof in eating. Further, the analogue turned into ricelike grains after 5 minutes of chewing, thus being easy to eat like that of the Example c3.

Example c5

A chewing gum analogue was prepared in the same manner as that of Example c3 except that active gluten powder was used instead of the gliadin-rich fraction. The organoleptic examination of the analogue revealed that the analogue was easy to eat like that of Example c3.

Example c6

70 g of the gliadin-rich fraction prepared in Referential Example c1 was sufficiently mixed with 30 g of pulverized gelatin and 0.8 g of a transglutaminase preparation, followed by the addition of 70 g of water with its pH adjusted to 6.5. The obtained mixture was kneaded, followed by the addition of 100 g of sugar and a perfume and a dye, each in proper amounts. The obtained mixture was kneaded and rolled into a sheet having a thickness of 1.5 mm. This sheet was kept at 55° C. for 30 minutes and thereafter exposed to steam to deactivate the enzyme. The water present on the surface of the sheet was removed and the resulting sheet was cut. Thus, a chewing gum analogue was obtained.

The chewing gum analogue was organoleptically evaluated. The analogue had a feel similar to that of chewing gum during eating and turned into ricelike grains with the lapse of chewing time, thus being very easy to eat like that of Example c3.

Referential Example b1 (Preparation of fraction 1)

Wheat gluten (activated gluten powder, 1 kg) was dissolved and dispersed in 8 l of a 70% by volume aqueous solution of ethanol. The obtained dispersion was stirred with propellers at room temperature for 2 hours to conduct extraction. The extraction mixture was centrifuged to give a precipitate. This precipitate was recovered, frozen as such, dried in a vacuum evaporator, and pulverized to give about 700 g of a glutenin-rich fraction. This fraction is hereinafter referred to as "fraction 1".

The properties of fraction 1 are as follows:

water content: 5%, protein: 75%, glutenin content: 90% (based on the protein), pH of a solution of 1 part thereof in 40 parts of water: 6.8, acidity with acetic acid: 0.6%.

Referential Example b2 (fraction 2)

In a similar manner to that of Referential Example b1, a precipitate was obtained from 1 kg of wheat gluten (activated gluten powder) by the use of an acidic aqueous solution of ethanol prepared by dissolving 3 g of citric acid in 10 l of a 15% by volume aqueous solution of ethanol. About 4 l of water was added to the precipitate and the obtained mixture was dispersed with a homomixer and spray-dried. Thus, 630 g of a glutenin-rich fraction was obtained as a powder. This fraction is hereinafter referred to as "fraction 2".

The properties of fraction 2 are as follows:

water content: 4%, protein: 76%, glutenin content: 60% (based on the protein), pH of a solution of 1 part thereof in 40 parts of water: 4.3, acidity with citric acid: 0.9%.

Examples b1 and b2 and Comparative Examples b1 and b2

1.7 times (by weight) as much water was added to each of 100 g of soft flour (Comparative Example b1), a mixture of 90 g of soft flour with 10 g of activated gluten powder (Comparative Example b2), a mixture of 90 g of soft flour with 10 g of the fraction 1 Example b1) and a mixture of 90 g of soft flour with 10 g of the fraction 2 (Example b2). The obtained mixtures were each stirred with a propeller mixer to give batters.

Each of the batters was put in a thermostatic water bath at 20° C. and examined for appearance and viscosity (with a Brookfield viscometer mfd. by Tokyo Keiki K. K.) under stirring with a propeller mixer (10 to 15 rpm). The results are given in Table 1. As shown in the Table 1, the batters of Examples b1 and b2 were stable even after a long time of stirring.

TABLE b1

|  | Comp. Ex. b1 | Comp. Ex. b2 | Ex. b1 | Ex. b2 |
|---|---|---|---|---|
| at the initiation of stirring | 820 cp | 1,018 cp | 1,530 cp | 1,880 cp |
| after 30 min. | 1,830 cp | 2,340 cp | 1,530 cp | 1.670 cp |
| after 80 min. | 960 cp | 1,850 cp | 1,520 cp | 1,670 cp |
| after 90 min. | 800 cp | 1,200 cp | 1,510 cp | 1,665 cp |
| after 120 min. | 760 cp | 990 cp | 1,510 cp | 1,685 cp |
| Appearance | separated after 30 min | separated after 30 min | not separated even after 120 min. | not separated even after.120 min. |

Examples b3 and b4 and Comparative Examples b3 and b4

Tempuras of carrot and prawn were experimentally made by the use of the batters prepared in Examples b1 and b2 and Comparative Examples b1 and b2. The fat frying was conducted at 180° C. for 3 to 4 minutes. Each tempura was eaten just after frying and after 1 and 3 hours after frying to conduct organoleptic evaluation. The results are given in Table b2. The batter used is given in parentheses. As understood from the results given in Table b2, the coatings of Examples b3 and b4 exhibited excellent palatability accompanied with crispiness in eating.

TABLE b2

|  | Just after | after 1 hr. | after 3 hr. |
|---|---|---|---|
| Comp. Ex. b3 (Comp. Ex. b1) | crispy and good-tasting one | heavy one which lacks crispiness | sticky and heavy one |
| Comp. Ex. b4 (Comp. Ex. b2) | hard one which does not taste good .and lacks crispiness | hard one which does not taste good | one which does not taste good, though not sticky |
| Ex. b3 (Ex.b1) | *crispy and good-tasting one crispiness | good-tasting one which retains crispiness | non-sticky one which somewhat retains |
| Ex. b4 (Ex. b2) | do. | do. | do. |

Example b5 and Comparative Example b5

1.5 times as much water was added to each of 100 g of soft flour (Comp. Ex. b5) and a mixture of 90 g of soft flour with 10 g of the fraction 2 (Example b5) to prepare batters. These batters were each stirred at 15° C. for one hour. Creamy croquettes were experimentally made by the use of the resulting batters. Although about 30% of the croquettes made with the batter of Comparative Example b5 suffered from the rupture of coating, none of the croquettes made with the batter of Example b5 suffered from it.

Among the croquettes not suffering from the rupture of coating, those of Example b5 had a crispy and good-tasting coating, though those of Comparative Example b5 had a hard coating.

Example b6 and Comparative Example b6

1.5 times as much water was added to each of 100 g of soft flour (Comparative Example b6) and a mixture of 90 g of soft flour with 10 g of the fraction 2 (Example b6) to prepare batters. These batters were each treated in the same manner as that of Example b5. Fried breaded pork cutlets were experimentally made by the use of the resulting batters and examined for the adhesion of coating to sliced pork. The fried breaded pork cutlets of Example b6 were so excellent in adhesion that no hollow was left between the sliced pork and the coating, though those of Comparative Example b6 were so poor in adhesion that a hollow was left between them. Referential Example d1 (separation of glutenin fraction)

Activated wheat gluten powder (1 kg) was extracted with an acidic aqueous solution of ethanol prepared by dissolving 2 g of citric acid in 10 l of a 10% by volume aqueous solution of ethanol at room temperature for 2 hours. The resulting extraction mixture was centrifuged to give a precipitate. 4 l of water was added to the precipitate and the obtained mixture was dispersed with a homomixer and spray-dried to give 360 g of a glutenin fraction as a dry powder.

The properties of this fraction are as follows:

water content: 4%, protein content: 76%, glutenin content; 84% (based on the protein), gliadin content: 10% (based on the protein), pH of aqueous solution of 1 part of the fraction in 40 parts of water: 4.3, acidity with citric acid: 2.8%.

Referential Example d2

(separation of glutenin)

Activated gluten powder (1 kg) was extracted with a 70% by volume aqueous solution of ethanol. The obtained residue was dissolved in a dilute aqueous solution of sodium hydroxide and the obtained mixture was filtered. The obtained filtrate was neutralized with dilute hydrochloric acid to give a precipitate. This precipitate was repeatedly washed with a 70% by volume aqueous solution of ethanol. The resulting precipitate was dried and pulverized to give 370 g of powdery glutenin.

The properties of the powdery glutenin are as follows:

water content: 3%, protein content: 90%, glutenin content: 99% (based on the protein), pH of aqueous solution of 1 part of the powder in 40 parts of water: 6.7, acidity with hydrochloric acid: below 0.1.

Example d1 and Comparative Examples d1 to d3

A baking test was conducted by experimentally making bread according to the formulations (each amount shown by part by weight) specified in Table d1 by the direct dough process. The test results were evaluated by examined the volume and specific volume of the bread. The results are given in Table d2. It can be understood from the results that the glutenin fraction according to the present invention is effective in improving the expansibility of dough.

TABLE d1

|  | Ex. d1 | Comp. Ex. d1 | Comp. Ex. d2 | Comp. Ex. d3 |
|---|---|---|---|---|
| strong wheat flour | 100 | 100 | 100 | 100 |
| glutenin fraction | 1 | — | — | — |
| glutenin | — | — | 2 | — |
| activated gluten powder | — | — | — | 2 |
| yeast | 2 | 2 | 2 | 2 |
| yeast food | 0.1 | 0.1 | 0.1 | 0.1 |
| common salt | 2 | 2 | 2 | 2 |
| sugar | 4 | 4 | 4 | 4 |
| oil or fat | 5 | 5 | 5 | 5 |
| skim milk powder | 1 | 1 | 1 | 1 |
| water | 61 | 60 | 62 | 62 |

TABLE d2

|  | Ex. d1 | Comp. Ex. d1 | Comp. Ex. d2 | Comp. Ex. d3 |
|---|---|---|---|---|
| volume after baking (cc) | 1,810 | 1,550 | 1,690 | 1,680 |
| specific volume (cc/g) | 5.36 | 4.47 | 4.91 | 4.89 |

Examples d2 and d3

In the same way as Example d1, a baking test was conducted according to the formulations specified in Table d3 wherein the glutenin fraction is used together with an emulsifying agent (HLB of sucrose fatty acid ester: 15), and examined. The results are given in Table d4 together with those of Example d1. It can be understood from the results that the simultaneous use of the glutenin fraction with an emulsifying agent can further improve the expansibility.

TABLE d3

|  | Ex. d1 | Ex. d2 | Ex. d3 |
|---|---|---|---|
| strong wheat flour | 100 | 100 | 100 |
| glutenin fraction | 1 | 0.5 | 0.5 |
| succinic monoglyceride | — | 0.3 | — |
| sucrose fatty acid ester | — | — | 0.3 |
| yeast | 2 | 2 | 2 |
| yeast food | 0.1 | 0.1 | 0.1 |
| common salt | 2 | 2 | 2 |
| sugar | 4 | 4 | 4 |
| skim milk powder | 3 | 3 | 3 |
| water | 61 | 61 | 61 |

TABLE d4

|  | Ex. d1 | Ex. d2 | Ex. d3 |
|---|---|---|---|
| volume after baking (cc) | 1,810 | 1,840 | 1,850 |
| specific volume (cc/g) | 5.36 | 5.50 | 5.51 |

Example d4

In the same way as Example d1, a baking test was conducted according to the formulation specified in Table d5. The glutenin paste used as the glutenin fraction was prepared by wetting glutenin with a 0.6% aqueous solution of sodium carbonate and adjusting the pH of the mixture to 6.7. The paste had a water content of 65%. The results are given in Table d6 together with those of Comparative Example d2. It can be understood from the results that the glutenin paste has also an effect equivalent to that of the powdery glutenin fraction of Example d1.

TABLE d5

|  | Ex. d4 | Comp. Ex. d2 |
|---|---|---|
| strong wheat flour | 100 | 100 |
| glutenin paste | 2.5 | — |
| glutenin | — | 2 |
| yeast | 2 | 2 |
| yeast food | 0.1 | 0.1 |
| common salt | 2 | 2 |
| sugar | 4 | 4 |
| oil or fat | 5 | 5 |
| skim milk powder | 1 | 1 |
| water | 80 | 82 |

TABLE d6

|  | Ex. d4 | Comp. Ex. d2 |
|---|---|---|
| volume after baking (cc) | 1,820 | 1,690 |
| specific volume (cc/g) | 5.38 | 4.91 |

Example d5

In the same way as Example d1, a baking test was conducted according to the formulation specified in Table d7 by using the glutenin fraction and wheat starch. The gliadin content of the bread was calculated from the amounts of the raw materials and the obtained bread was also tested organoleptically. The calculation and the test were conducted also with respect to the bread of Comparative Example d1. The results are given in Table d8. It can be understood from the results that the bread of Example d5 was equivalent to an ordinary one in flavor and had a reduced gliadin content.

TABLE d7

|  | Ex. d5 | Comp. Ex. d1 |
|---|---|---|
| strong wheat flour | — | 100 |
| wheat starch flour | 84 | — |
| glutenin fraction | 16 | — |
| yeast | 2 | 2 |
| Yeast food | 0.1 | 0.1 |
| common salt | 2 | 2 |
| sugar | 4 | 4 |
| oil or fat | 5.5 | 5 |
| skim milk powder | — | 1 |
| emusifying agent | 1 | — |
| water | 61 | 60 |

TABLE d8

|  | Gliadin content | Organoleptic test |
|---|---|---|
| Ex. d5 | 1.2% | palatability nearly equivalent to that of |
| Comp. Ex. | 5.3% | the bread of Comp. Ex. 1 exhibited |

Examples d6 and d7 and Comparative Example d4

Powder mixes were prepared according to the formulations specified in Table d9 wherein the glutenin fraction was contained, and sponge cakes were experimentally made from the mixes and evaluated. As a control (Comparative Example d4), a powder mix was prepared without using the glutenin fraction and a sponge cake was made from the mix and evaluated. The evaluation of each cake was conducted by determining the volume and specific volume thereof and whipping time.

The sponge cakes were each made by mixing 50 parts by weight of whole egg with 25 parts by weight of water and 2 parts by weight of a foaming agent with a table cake mixer (mfd. by Kenwood Corporation), adding 100 parts by weight of each powder mix to the obtained mixture, whipping the resulting mixture until a batter having a specific gravity of 0.45 was formed, and baking the obtained batter, while the whipping time was determined during the make. The results are given in Table d10. It can be understood from the results that the batter containing the glutenin fraction exhibited high expansibility and could be whipped rapidly.

TABLE d9

|  | Ex. d6 | Ex. d7 | Comp. Ex. d4 |
| --- | --- | --- | --- |
| soft wheat flour | 45.0 | — | 45.5 |
| wheat starch flour | 4.5 | 47.0 | 4.5 |
| sugar | 45.0 | 45.0 | 45.0 |
| glutenin fraction | 0.5 | 3.0 | — |
| shortening powder | 4.0 | 4.0 | 4.0 |
| expanding agent | 1.0 | 1.0 | 1.0 |

TABLE d10

|  | Ex. d6 | Ex. d7 | Comp. Ex. d4 |
| --- | --- | --- | --- |
| whipping time (min) | 9 | 9 | 13 |
| volume (cc) | 378 | 390 | 318 |
| specific volume (cc/g) | 3.15 | 3.25 | 2.85 |

Referential Example e1
(separation of gliadin fraction)

Activated wheat gluten powder (1 kg) was extracted with an acidic aqueous solution of ethanol prepared by dissolving 2 g of citric acid in 10 l of a 10% by volume aqueous solution of ethanol, at room temperature for 2 hours. The resulting extraction mixture was centrifuged to recover the formed supernatant. This supernatant was spray-dried to give 360 g of a gliadin fraction as a dry powder.

The properties of the gliadin fraction are as follows:

water content: 4%, protein content: 90%, gliadin content: 80% (based on the protein), pH of aqueous solution of 1 part of the fraction in 40 parts of water: 3.9, acidity with citric acid: 4.5%.

Referential Example e2
(separation of gliadin 1 and 2)

Activated gluten powder (1 kg) was extracted with a 70% by volume aqueous solution of ethanol to give crude gliadin. This crude gliadin was freed from the solvent in a vacuum to give a dry product, which was further pulverized to give 180 g of crude powdery gliadin (hereinafter referred to as "gliadin 1"). Separately, crude gliadin prepared in the same manner as that described above was subjected to precipitation with 99.5% by volume ethanol, and the obtained precipitate was further dissolved in a 70% by volume aqueous solution of ethanol. This precipitation-dissolution cycle was repeated to obtain pure gliadin, which was dried in a vacuum to give 60 g of powdery gliadin (hereinafter referred to as "gliadin 2").

The properties of the gliadin are as follows:

|  | Gliadin | |
| --- | --- | --- |
|  | 1 | 2 |
| water content: | 3% | 3% |
| protein content: | 90% | 95% |
| gliadin content (based on the protein): | 95% | 99% |
| pH of aqueous solution of 1 part of the gliadin in 40 parts of water: | 6.7 | 6.8 |
| acidity with hydrochloric acid: | 0.1 or below | 0.1 or below. |

Example e1 and Comparative Examples e1 to e4

Bread was experimentally made by the direct dough process according to the formulation specified in Table e1 by part by weight, and examined for the volume after baking and specific volume. Further, the crumb hardness of each bread was measured over a lapse of time with a rheometer. The results are given in Table e2. The crumb hardness is shown also by the ratio calculated by taking the initial crumb hardness of bread of Example e1 as 100. It can be understood that the gliadin fraction is effective in enhancing the expansion of bread and in preventing the aging thereof.

TABLE e1

|  | Ex. e1 | Comp. Ex. e1 | Comp. Ex. e2 | Comp. Ex. e3 | Comp. Ex. e4 |
| --- | --- | --- | --- | --- | --- |
| strong wheat flour | 100 | 100 | 100 | 100 | 100 |
| gliadin fraction | 2 | — | — | — | — |
| gliadin 1 | — | — | 2 | — | — |
| gliadin 2 | — | — | — | 2 | — |
| activated gluten powder | — | — | — | — | 2 |
| yeast | 2 | 2 | 2 | 2 | 2 |
| yeast food | 0.1 | 0.1 | 0.1 | 0.1 | 0.1 |
| common salt | 2 | 2 | 2 | 2 | 2 |
| sugar | 4 | 4 | 4 | 4 | 4 |
| oil or fat | 5 | 5 | 5 | 5 | 4 |
| skim milk powder | 3 | 3 | 3 | 3 | 3 |
| water | 64 | 60 | 62 | 62 | 63 |

TABLE e2

|  | Ex. e1 | Comp. Ex. e1 | Comp. Ex. e2 | Comp. Ex. e3 | Comp. Ex. e4 |
| --- | --- | --- | --- | --- | --- |
| volume after baking (cc) | 1,750 | 1,550 | 1,620 | 1,600 | 1,570 |
| specific volume (cc/g) | 5.18 | 4.47 | 4.68 | 4.64 | 4.55 |

TABLE e2-continued

|  | Ex. e1 | Comp. Ex. e1 | Comp. Ex. e2 | Comp. Ex. e3 | Comp. Ex. e4 |
|---|---|---|---|---|---|
| crumb hardness (g) | | | | | |
| at starting | 182 | 185 | 211 | 195 | 215 |
| (ratio) | (100) | (102) | (116) | (107) | (118) |
| after 24 hr | 230 | 350 | 278 | 270 | 320 |
| (ratio) | (126) | (192) | (153) | (148) | (176) |
| after 48 hr | 302 | 464 | 366 | 356 | 436 |
| (ratio) | (166) | (255) | (201) | (196) | (240) |
| after 72 hr | 354 | 556 | 440 | 432 | 506 |
| (ratio) | (194) | (305) | (242) | (237) | (298) |

Example e2

Part of the baked bread made in the Example e1 was frozen at −20° C. in a state put in a vinyl bag to prevent drying. The bread was stored as such at that temperature for one month and thereafter thawed out at room temperature. The resulting bread was examined for crumb hardness with the lapse of time. In a similar manner to that described above, the ratio of each crumb hardness was also calculated. The results are given in Table e3. It can be understood from the results that the gliadin fraction according to the present invention is effective in preventing the crumbs from hardening from freezing.

TABLE e3

|  | Ex. e1 | Comp. Ex. e1 | Comp. Ex. e2 | Comp. Ex. e3 | Comp. Ex. e4 |
|---|---|---|---|---|---|
| at thawing | 190 | 230 | 246 | 215 | 230 |
| (ratio) | (100) | (121) | (129) | (113) | (121) |
| after 24 hr | 287 | 485 | 398 | 389 | 407 |
| (ratio) | (151) | (255) | (209) | (205) | (214) |

Examples e3 to e5 and Comparative Example e5

In the same way as Example e1, bread was experimentally made according to the formulations specified in Table e4 and evaluated. As a control (Comparative Example e5), bread was further made in the same manner as that employed above except that an emulsifying agent was used without using the gliadin fraction. The results are given in Table e5. Each crumb hardness is shown also by the ratio calculated by taking the initial crumb hardness of bread of Comparative Example e5 as 100. It can be understood from the results that when both an emulsifying agent and a pH regulator are used simultaneously with the gliadin fraction, the aging of the bread can be prevented, even by the use of a reduced amount of the gliadin fraction.

TABLE e4

|  | Ex. e3 | Ex. e4 | Ex. e5 | Comp. Ex. e5 |
|---|---|---|---|---|
| strong wheat flour | 100 | 100 | 100 | 100 |
| gliadin fraction | 1.5 | 1.0 | 1.5 | — |
| lactic monoglyceride | 0.5 | 0.5 | — | 0.5 |
| sodium carbonate | — | 0.08 | 0.08 | — |
| yeast | 2 | 2 | 2 | 2 |
| yeast food | 0.1 | 0.1 | 0.1 | 0.1 |

TABLE e4-continued

|  | Ex. e3 | Ex. e4 | Ex. e5 | Comp. Ex. e5 |
|---|---|---|---|---|
| common salt | 2 | 2 | 2 | 2 |
| oil or fat | 5 | 5 | 5 | 5 |
| sugar | 4 | 4 | 4 | 4 |
| skim milk powder | 3 | 3 | 3 | 3 |
| water | 83 | 82 | 63 | 60 |

TABLE e5

|  | Ex. e3 | Ex. e4 | Ex. e5 | Comp. Ex. e5 |
|---|---|---|---|---|
| volume after baking (cc) | 1,770 | 1,750 | 1,740 | 1,600 |
| specific volume (cc/g) | 5.23 | 5.18 | 5.12 | 4.71 |
| crumb hardness (g) | | | | |
| at starting | 180 | 185 | 187 | 188 |
| (ratio) | (97) | (99) | (101) | (100) |
| after 24 hr | 215 | 223 | 225 | 330 |
| (ratio) | (116) | (120) | (121) | (177) |
| after 48 hr | 277 | 283 | 286 | 430 |
| (ratio) | (149) | (152) | (154) | (230) |
| after 72 hr | 336 | 340 | 338 | 498 |
| (ratio) | (181) | (183) | (182) | (268) |

Examples e6 and e7 and Comparative Examples e6 and e7

Cake mixes containing the gliadin fraction were prepared according to the formulations specified in Table 6, and sponge cakes were experimentally made from the mixes and evaluated. As controls, cakes were also made from a mixture not containing the gliadin fraction (Comparative Example 6) and a mixture containing gluten instead of the gliadin fraction (Comparative Example e7). The obtained sponge cakes were evaluated for volume, specific volume, and change in the crumb hardness of cake after baking with the lapse of time. Further, after the cakes had been frozen and stored at −20° C. and then thawed out, they were examined for crumb hardness. The results are given in Table e7. In the Table e7, each crumb hardness is shown also by the ratio calculated by taking the initial crumb hardness of the cake of Example e6 as 100. Symbol "−" represents hard crumb unsuitable for cake. It can be understood from the results that the cakes containing the gliadin fraction are effectively prevented from aging and denaturing during freezing.

The sponge cakes were each made by mixing 50 parts by weight of whole egg with 25 parts by weight of water and 2 parts by weight of a foaming agent with a table cake mixer (mfd. by Kenwood Corporation), adding 100 parts by weight of each cake mix to the obtained mixture, whipping the resulting mixture until a batter having a specific gravity of 0.45 was formed, and thereafter baking the batter.

TABLE e6

|  | Ex. e6 | Ex. e7 | Comp. Ex. e6 | Comp. Ex. e7 |
|---|---|---|---|---|
| soft wheat flour | 43.0 | — | 45.0 | 43.0e |
| wheat starch | 5.0 | 43.8 | 5.0 | 4.5 |
| gliadin fraction | 2.0 | 6.0 | — | — |
| gluten | — | — | — | 2.0 |
| sugar | 45.0 | 45.0 | 45.0 | 45.0. |
| shortening powder | 4.0 | 4.0 | 4.0 | 4.0 |
| expanding agent | 1.0 | 1.2 | 1.0 | 1.0 |

TABLE e7

|  | Ex. e6 | Ex. e7 | Comp. Ex. e8 | Comp. Ex. e7 |
|---|---|---|---|---|
| volume (cc) | 380 | 378 | 375 | 228 |
| specific volume (cc/g) | 3.17 | 3.15 | 3.13 | 1.90 |
| crumb hardness (g) |  |  |  |  |
| at starting | 240 | 236 | 230 | 600 |
| (ratio) | (106) | (98) | (98) | (250) |
| after 2 days | 345 | 348 | 378 | — |
| (ratio) | (144) | (145) | (157) | — |
| after 4 days | 355 | 350 | 470 | — |
| (ratio) | (148) | (148) | (196) | — |
| after 7 days | 360 | 359 | 500 | — |
| (ratio) | (150) | (150) | (208) | — |
| after one-month storage in freezed state | 255 | 250 | 420 | — |
| (ratio) | (108) | (104) | (175) | — |

Example e8 and Comparative Examples e8 and e9

In a similar manner to that of Example e6, a low-calorie sponge cake mix was experimentally prepared by the use of the gliadin fraction and a natural gum according to the formulation specified in Table e8, and evaluated. As controls, a cake mix not containing the gliadin fraction (Comparative Example e8) and one containing neither the gliadin fraction nor natural gum (Comparative Example e9) were prepared and evaluated. The results are given in Table e9. Each crumb hardness is shown also by the ratio calculated by taking the initial crumb hardness of cake of Example e8 as 100. It can be understood from the results that a sponge cake prepared by the use of both a natural gum and the gliadin fraction is effectively prevented from aging and denaturing during freezing, even when it contains a reduced amount of sugar.

TABLE e8

|  | Ex. e8 | Comp. Ex. e8 | Comp. Ex. e9 |
|---|---|---|---|
| soft wheat flour | 50.0 | 56.0 | 56.0 |
| processed wheat starch flour | 8.7 | 8.7 | 9.0 |
| gliadin fraction | 6.0 | — | — |
| guar gum | 0.3 | 0.3 | — |
| reducing maltose powder | 30.0 | 30.0 | 30.0 |
| shortening powder | 4.0 | 4.0 | 4.0 |
| expanding agent | 1.0 | 1.0 | 1.0 |

TABLE e9

|  | Ex. e8 | Comp. Ex. e6 | Comp. Ex. e7 |
|---|---|---|---|
| volume (cc) | 375 | 345 | 332 |
| specific volume (cc/g) | 3.13 | 2.87 | 2.78 |
| crumb hardness (g) |  |  |  |
| at starting | 240 | 230 | 235 |
| (ratib) | (100) | (98) | (98) |
| after 2 days | 290 | 370 | 385 |
| (ratio) | (121) | (154) | (169) |
| after 4 days | 314 | 487 | 499 |
| (ratio) | (131) | (203) | (268) |
| after 7 days | 348 | 590 | 612 |
| (ratio) | (145) | (248) | (255) |

Example e9 and Comparative Example e10

Dough was experimentally prepared by the use of freeze-resistant yeast according to the formulation specified in Table e10 by the direct dough method. As a control, dough not containing the gliadin fraction was also prepared. Each dough was divided, frozen at −40° C. in a packaged state so as to prevent the evaporation of water from the dough, and stored at −20° C. for 30 days. Then, the resulting dough was thawed out, finally fermented in a proofer (38° C., humidity: 60%), and baked. The obtained bread was examined for volume and specific volume. Further, in the same manner as that described above, the dough before freezing (i.e., unfrozen dough) was also baked and the obtained bread was evaluated. The results are given in Table e11. It can be understood from the results that the gliadin fraction according to the present invention is effective in preventing frozen dough from denaturing during freezing.

TABLE e10

|  | Ex. e9 | Comp. Ex. e10 |
|---|---|---|
| strong wheat flour | 90 | 100 |
| gliadin fraction | 10 | — |
| Succinic monoglyceride | 1 | — |
| yeast | 7 | 7 |
| yeast food | 0.1 | 0.1 |
| Common salt | 2 | 2 |
| sugar | 5 | 5 |
| oil or fat | 5 | 5 |
| skim milk powder | 2 | 2 |
| water | 65 | 60 |

TABLE e11

|  | Ex. e9 | | Ex. e10 | |
|---|---|---|---|---|
|  | before freezing | after storage in frozen state | before freezing | after storage in frozen state |
| volume after baking (cc) | 1,780 | 1,700 | 1,820 | 1,220 |
| specific volume (cc/g) | 5.28 | 5.05 | 4.e7 | 3.52 |
| reduction in specific volume (%) | — | 4.4 | — | 24.6 |

Referential Example f1
(preparation of fraction 1)

1 kg of wheat gluten (powdery active gluten) was dissolved and dispersed in 8 liters of a 60% by volume aqueous ethanol solution, and agitated by means of a propeller at room temperature for 2 hours to thereby effect extraction. The extract was centrifuged by means of a centrifugal separator, and the resultant supernatant was dried by means of a vacuum concentrator and a vacuum drier. The thus obtained dry residue was pulverized by means of a pulverizer, thereby obtaining about 300 g of a fraction composed mainly of gliadin (hereinafter referred to as "fraction 1").

The properties of the obtained fraction 1 were as follows.

Water content: 5%,

Protein content: at least 90%,

Gliadin content: 90%, pH of 1/40 aqueous solution: 6.8,

Acidity with acetic acid: 0.6%.

Referential Example f2
(preparation of fraction 2)

1 kg of wheat gluten (powdery active gluten) was extracted with the use of an acid aqueous ethanol solution obtained by dissolving 3 g of citric acid in 10 l of a 15% by volume aqueous ethanol solution in the same manner as in Referential Example f1. The resultant extract was concentrated in a vacuum until a solid content of 10 to 20% was achieved, and dried by means of a spray drier, thereby obtaining about 370 g of a powdery fraction composed mainly of gliadin (hereinafter referred to as "fraction 2").

The properties of the obtained fraction 2 were as follows.

Water content: 4%,

Protein content: at least 75%,

Gliadin content: 60%,

Glutenin content: 15%, pH of 1/40 aqueous solution: 4.1,

Acidity with citric acid 0.8%.

Examples f1–f2 and Comparative Examples f1–f3

30 g of salt was added to 1 kg of frozen ground meat, and the resultant mixture was ground for 25 min while keeping the temperature thereof at 10° C. or lower. 50 g of potato starch and 20 g of each of fraction 1 (Example f1) and fraction 2 (Example f2) were dispersed in water and added 5 min before the completion of the grinding. 300 g of ice and ice water were used through the entire process. In place of the addition of the potato starch and each of the fractions, like preparations were performed by adding to the ground meat only the potato starch without the addition of any of the fractions (Comparative Example f1) and adding the potato starch together with the powdery active gluten used in Referential Example f1 as a substitute for the fractions (Comparative Example f2). Further, similar preparations were prepared by adding commercially available emulsification-active gluten [A-Glu SS, Glico Foods Co., Ltd.] (Comparative Example f3). After the completion of the grinding, each of the obtained ground meats was immediately put in a polyvinyl chloride film of 60 mm in width and 250 mm in length, and tied by a chipper.

After the tying, each of the meat products was subjected to "sitting" in a thermostatic oven set at 40° C. for 90 min, and heated in a 85° C. water bath for 40 min. Immediately after the heat treatment, each of the meat products was cooled with cold water to thereby lower the temperature of the center of the meat product to 30° C. or below, and allowed to stand still in a refrigerator for 12 hr. For the quality assessment, the rupture load (W value, g) and the rupture elongation (L value, cm) thereof were measured by the use of a rheometer (Rheometer NRM20 manufactured by Fudo Kogyo Co., Ltd.), and the springiness was calculated therefrom. The degree of improvement relative to the values of Comparative Example f1 was calculated according to the following formulae:

Degree of improvement for L value (%)=[(L value of each sample−L value of Comp. Ex. 1)/L value of Comp. Ex. 1]×100

Degree of improvement for WL value (%)=[(WL value of each sample−WL value of Comp. Ex. 1) /WL value of Comp. Ex. 1]×100

Five test pieces for quality assessment were prepared by removing the end portion of each sample in a width of 1 cm and cutting a piece of 2.5 cm in width off the sample. The W and L values of each of the samples were determined with the use of a spherical plunger of 5 mm in diameter, and three W and L values, excluding those of the maximum and the minimum, were averaged. Results are shown in Table f1.

TABLE f1

|  | W value (g) | L value (cm) | WL value | Degree of improvement (%) | |
|---|---|---|---|---|---|
|  |  |  |  | L value | WL value |
| Comp. Ex. f1 | 800 | 0.96 | 768 | 0.0 | 0.0 |
| Comp. Ex. f2 | 830 | 0.93 | 813 | −3.1 | 5.9 |
| Comp. Ex. f3 | 825 | 0.99 | 816 | 3.1 | 8.3 |
| Ex. f1 | 886 | 1.16 | 1,026 | 20.8 | 33.6 |
| Ex. f2 | 904 | 1.11 | 1,003 | 15.8 | 30.8 |

Table f1 shows the improvement of the rupture elongation by the fraction used in the present invention, even at temperatures adopted in the conventional production of kamaboko.

Examples f3–f4 and Comparative Examples f4–f7

30 g of salt was added to 800 g of frozen ground meat and 200 g of tuna dark, and ground with the use of a silent cutter. 80 g of lard, 20 g of sugar, 100 g of starch, 2 g of smoked liquid and 37 g of seasoning together with 50 g of each the fraction 1 (Example 3) and the fraction 2 (Example f4) were added, and kneaded together. Similar preparations were prepared with the use of each of powdery egg white (Comparative Example f4), spray-dried powdery active gluten (Comparative Example 5) and denatured gluten [A-Glu U, Glico Foods Co., Ltd.] (Comparative Example f6) in place of the fraction 1, and none of them (Comparative Example f7) in the same manner as in Example f3. After the kneading, each of the obtained pastes was packed into a casing for fish meat sausage, tied, heated at 120° C. for 4 min, immediately cooled, and evaluated in the same manner as in Example f1. Results are shown in Table f2.

TABLE f2

|  | W value (g) | L value (cm) | WL value | Degree of improvement (%) K value | Degree of improvement (%) WL value |
|---|---|---|---|---|---|
| Comp. Ex. f7 | 180 | 0.30 | 55.5 | 0.0 | 0.0 |
| Comp. Ex. f4 | 185 | 0.29 | 53.7 | −3.0 | −3.2 |
| Comp. Ex. f5 | 205 | 0.30 | 61.5 | 0.0 | 10.5 |
| Comp. Ex. f6 | 200 | 0.31 | 62.0 | 3.3 | 11.7 |
| Ex. f3 | 206 | 0.34 | 74.1 | 20.0 | 33.5 |
| Ex. f4 | 200 | 0.36 | 68.0 | 13.3 | 22.5 |

Table f2 shows the improvements of not only the rupture elongation but also the springiness (WL value), even after heat treatment at high temperatures attained in the above Examples.

Examples f5–f6 and Comparative Examples f8–f10

200 g of lard, 25 g of salt, 200 g of ice, 2.5 g of seasoning, 6.5 g of spice, 2.2 g of potassium sorbate and 30 g of fraction 1 together with each of pH adjusting agents for a pH value of 6.8 (Example f5) and for a pH value of 6.3 (Example f6) were added to 600 g of cured lean pork and 400 g of lean beef, ground with the use of a silent cutter, and kneaded together. Like preparations were performed in the same manner as in Example 5 by omitting the addition of the fraction 1 and pH adjusting agents (Comparative Example f8), effecting the addition of the pH adjusting agent without the addition of the fraction 1 (pH value of 6.3, Comparative Example f9), and adding the denatured gluten employed in Comparative Example f6 in place of the fraction 1 (Comparative Example f10). After the kneading, each of the obtained pastes was packed into a swine intestine, heated at 95° C. for 20 min, and dry-smoked to thereby obtain a frankfurter. With respect to each of the samples, the evaluation was made in the same manner as in Example f1, and further, the increase or decrease of general living bacteria during the preservation in a thermostatic bath set at 15° C. was measured. Results are shown in Table f3 and Table f4 (general viable cell count). Lactic acid and sodium lactate were used as the pH adjusting agents.

TABLE f2

|  | pH | W value (g) | L value (cm) | WL value | Degree of improvement (%) L value | Degree of improvement (%) WL value |
|---|---|---|---|---|---|---|
| Comp. Ex. f8 | 6.9 | 310 | 0.26 | 80.6 | 0.0 | 0.0 |
| Comp. Ex. f9 | 6.3 | 290 | 0.24 | 69.8 | −17.7 | −13.6 |
| Comp. Ex. f10 | 6.8 | 340 | 0.29 | 98.8 | 11.5 | 22.3 |
| Ex. f5 | 6.8 | 345 | 0.35 | 120.8 | 34.6 | 49.9 |
| Ex. f8 | 8.3 | 340 | 0.34 | 115.8 | 30.7 | 43.4 |

TABLE f4

|  | 0 day | 5 days | 10 days | 15 days |
|---|---|---|---|---|
| Comp. Ex. f8 | 300 or less | $5 \times 10^5$ | $6 \times 10^7$ | — |
| Comp. Ex. f9 | 300 or less | $4 \times 10^3$ | $7 \times 10^4$ | $2 \times 10^7$ |
| Comp. Ex. f10 | 300 or less | $4 \times 10^5$ | $7 \times 10^7$ | — |
| Ex. f8 | 300 or less | $3 \times 10^3$ | $6 \times 10^4$ | $4 \times 10^6$ |

Tables f3 and f4 show that the product of Example f6 did not exhibit any loss of rupture elongation, even after heat treatment at high temperatures at a lowered pH value, and that sorbic acid exerted a preserving effect because the pH was as low as 6.3.

Example f7

A mixture of 60% of fraction 2, 10% of carrageenan, 20% of egg white and 10% of powdery fat or oil (fat or oil content: 50%) was prepared. 30 g of the mixture was added to 1 kg of beef and pork ground together, 300 g of cut onion, 150 g of bread crumbs, 1.5 g of salt and 1 g of seasoning and spice, kneaded together well, and shaped into oval hamburger steaks each weighing 100 g. These were heated in a steamer for 30 min, and each of the heated steaks, together with 30 g of hamburger steak sauce, was put into a pouch and sterilized at 110° C. for 15 min. The change in weight of each of the hamburger steaks caused by the steaming (steaming yield) was measured and the palatability of each of the pouch-packed meat products were determined by organoleptic evaluation. Results are shown in Table f5.

Comparative Examples f11–f12

Hamburger steaks were prepared in the same manner as in Example f7, except that no fraction 2 was added (Comparative Example f11), and that 18 g of powdery active gluten and 6 g of egg white were added as a substitute for the fraction 2 (Comparative Example f12). The hamburger steaks were evaluated in the same manner as in Example f7, and results are shown in Table f5.

TABLE f5

|  | steaming yield | palatability of pouch-packed product |
|---|---|---|
| Comp. Ex. f11 | 79% | poor in shape retention, hard, and not tasty. |
| Comp. Ex. f12 | 82% | slightly improved in shape retention, but extremely hard and not tasty. |
| Ex. f7 | 95% | good in shape retention, springy, and tasty. |

Table f5 shows that the product of the Example has excellent steaming yield, shape retention in pouch-packed form, and palatability.

Example f8 and Comparative Examples f13–f14

25 g of salt was added to 1 kg of frozen ground meat (grade SA), and grinding thereof was performed for 25 min while keeping the temperature of the meat at 10° C. or lower. 100 g of potato starch, 20 g of fraction 2 and 5 g of emulsifier preparation (10% of sorbitan monooleate, 10% of sucrose mono/dioleate and 4% of ethanol) were added 5 min before the completion of the grinding. The pH value thereof was adjusted with sodium phosphate. 300 g of ice and ice water were used through the entire process (Example f8). Like preparations were performed by omitting the additions of the fraction 2 and the emulsifier preparation (Comparative Example f13 ), omitting only the addition of the emulsifier preparation (Comparative Example f14), and omitting only the addition of the fraction 2 (Comparative Example f15) in the same manner as in Example f8.

After the completion of the grinding, each of the ground meats was immediately put in a polyvinyl chloride film of 60 mm in width and 250 mm in length, and tied by a clipper. After the tying, each of the meat products was subjected to "sitting" at 10° C. for 20 hr, and heated in a 85° C. water bath for 40 min. Immediately after the heat treatment, each of the products was cooled with cold water, and evaluated in the same manner as in Example f1. Results are shown in Table f6.

TABLE f6

|  | pH | W value (g) | L value (cm) | WL value |
| --- | --- | --- | --- | --- |
| Comp. Ex. f13 | 7.03 | 585 | 1.02 | 598 |
| Comp. Ex. f14 | 6.96 | 651 | 1.23 | 801 |
| Comp. Ex. f15 | 7.12 | 574 | 1.05 | 803 |
| Ex. f8 | 7.03 | 871 | 1.35 | 908 |

The results of Table f6 demonstrate the effect of the use of the fraction composed mainly of gliadin in combination with the emulsifier.

Example f9 and Comparative Examples f15–f16

Kamaboko was produced in the same manner as in Example f8, except that 10 g of transglutaminase preparation Activa TG-K (produced by Ajinomoto Co., Ltd.) was added so as to be homogeneously dispersed in place of 5 g of the emulsifier preparation (Example f9). Further, similar kamaboko preparations were prepared in the same manner as in Example f9 by omitting the additions of the fraction 2 and the transglutaminase preparation (Comparative Example f16), omitting only the addition of the transglutaminase preparation (Comparative Example f17), and omitting only the addition of the fraction 2 (Comparative Example f18). Each of the obtained kamaboko products was evaluated in the same manner as in Example f1, and results are shown in Table f7.

TABLE f7

|  | pH | W value (g) | L value (cm) | WL value |
| --- | --- | --- | --- | --- |
| Comp. Ex. f16 | 6.95 | 590 | 1.01 | 596 |
| Comp. Ex. f17 | 7.05 | 647 | 1.25 | 809 |
| Comp. Ex. f18 | 6.98 | 678 | 1.18 | 800 |
| Ex. f9 | 7.01 | 706 | 1.36 | 960 |

The results of Table f7 demonstrate the effect of the use of the fraction composed mainly of gliadin in combination with transglutaminase.

[What is claimed is]:

1. In a chewing gum analogue composition, the improvement comprising said composition containing a gliadin-containing fraction which was thermally treated at a water content of at least 10% and a pH of from 4 to 11, and transglutaminase.

2. The chewing gum analogue composition of claim 1, wherein the thermal treatment is conducted at a pH of from 5 to 8, a temperature of from 55° to 100° C. and a time of from 1 to 120 minutes.

3. In a chewing gum analogue composition, the improvement comprising said composition containing a product obtained by mixing gliadin or gluten with transglutaminase.

* * * * *